United States Patent [19]

Matsuzaki et al.

[11] Patent Number: 5,674,719

[45] Date of Patent: Oct. 7, 1997

[54] METHOD FOR PRODUCING MONOCLONAL ANTIBODIES SPECIFIC TO HAIR FOLLICLES

[75] Inventors: Takashi Matsuzaki, Hiroshima; Mutsumi Inamatsu, 7-6 Nishihonmachi, Saijo, Higashi-Hiroshima-shi, Hiroshima; Katsutoshi Yoshizato, Hiroshima, all of Japan

[73] Assignees: Research Development Corportion of Japan, Kawaguchi; Mutsumi Inamatsu, Higashi-Hiroshima, both of Japan

[21] Appl. No.: 339,262

[22] Filed: Nov. 10, 1994

[30] Foreign Application Priority Data

Nov. 12, 1993 [JP] Japan .................................. 5-283007

[51] Int. Cl.$^6$ .............................. C12N 15/02; C12N 5/12; C12P 21/08; C07K 16/28
[52] U.S. Cl. ...................... 435/172.2; 435/70.21; 435/240.27; 530/388.2
[58] Field of Search .......................... 435/172.2, 240.27, 435/70.21; 530/388.2

[56] References Cited

U.S. PATENT DOCUMENTS

| | | |
|---|---|---|
| 4,683,200 | 7/1987 | Hirohashi et al. ........... 435/68 |
| 4,722,899 | 2/1988 | Hamaoka et al. . |
| 5,171,685 | 12/1992 | McElwain et al. . |
| 5,272,258 | 12/1993 | Siegel et al. . |
| 5,425,937 | 6/1995 | Lichiwa et al. . |

OTHER PUBLICATIONS

Goding, Journal of Immunological Methods, vol. 39, pp. 285–308, 1980.

Borrebaeck, Journal of Immunological Methods, vol. 123, pp. 157–165 (1989).

Seaver, Genetic Engineering News, vol. 14, No. 14, pp. 10 and 21 (Aug. 1994).

Kohler et al., Nature, vol. 256, pp. 495–497 (1975).

French et al., The Journal of Cell Biology, vol. 102, pp. 1412–1418 (1986).

Tobin et al., The Journal of Investigative Dermatology, vol. 102, No. 5, pp. 721–724 (May 1994).

Mils, V. et al, J Histochem & Cytochem, 40(9):1329–1337, 1992.

Couchman, J.R. et al., J Invest Dermatol, 94:65–70, 1990.

Hamilton, E.H. et al, J Invest Dermatol, 96:666–672, 1991.

Ito, M. et al, J Invest Dermatol, 86:563–569, 1986.

*Primary Examiner*—Susan A. Loring
*Attorney, Agent, or Firm*—Wenderoth Lind & Ponack

[57] ABSTRACT

This invention provides a method for preparing hybridomas, which include the steps of: quickly and deeply freezing hair-bulbs of follicle isolated from a human or an animal of species A; immunizing an animal of species B by subcutaneously administering the hair-bulbs after being thawed out to the animal; re-immunizing the animal by intravenously and intraperitoneally administering liquid and solid components of hair-bulbs obtained by centrifugation of minced thawed hair-bulbs to the animal; fusing spleen cells or lymphoid cells isolated from the immunized animal with myeloma cells derived from an animal of species B or C, and cloning fusion cells which produce antibodies capable of specifically binding to the hair follicle of human or animal of species A. The hybridomas prepared by the above methods can produce monoclonal antibodies specifically recognizing hair follicle tissues, and these antibodies enable functional analysis of hair follicle in addition to development of new diagnostic and therapeutic means for abnormal hair development, alopecia, etc.

2 Claims, 8 Drawing Sheets

HAIR CYCLE

METHOD FOR PRODUCING MONOCLONAL ANTIBODIES SPECIFIC TO HAIR FOLLICLES

BACKGROUND OF THE INVENTION

1. Field of the Invention

This invention relates to a method for preparing hybridomas which produce monoclonal antibodies against hair follicle tissues, to the hybridomas obtained by the said method and to monoclonal antibodies produced by the said hybridomas.

The monoclonal antibodies obtainable by this invention are very effective markers of hair follicle tissues which are involved in the differentiation and growth of hairs. The antibodies also enable analysis of the function of each hair follicle tissue and/or specification of the hair cycle, and are useful for research and development of new diagnostic methods, therapeutic methods and therapeutic drugs, etc., for treatment of abnormal hair development and/or alopecia.

2. Description of Related Art

Figure 1:
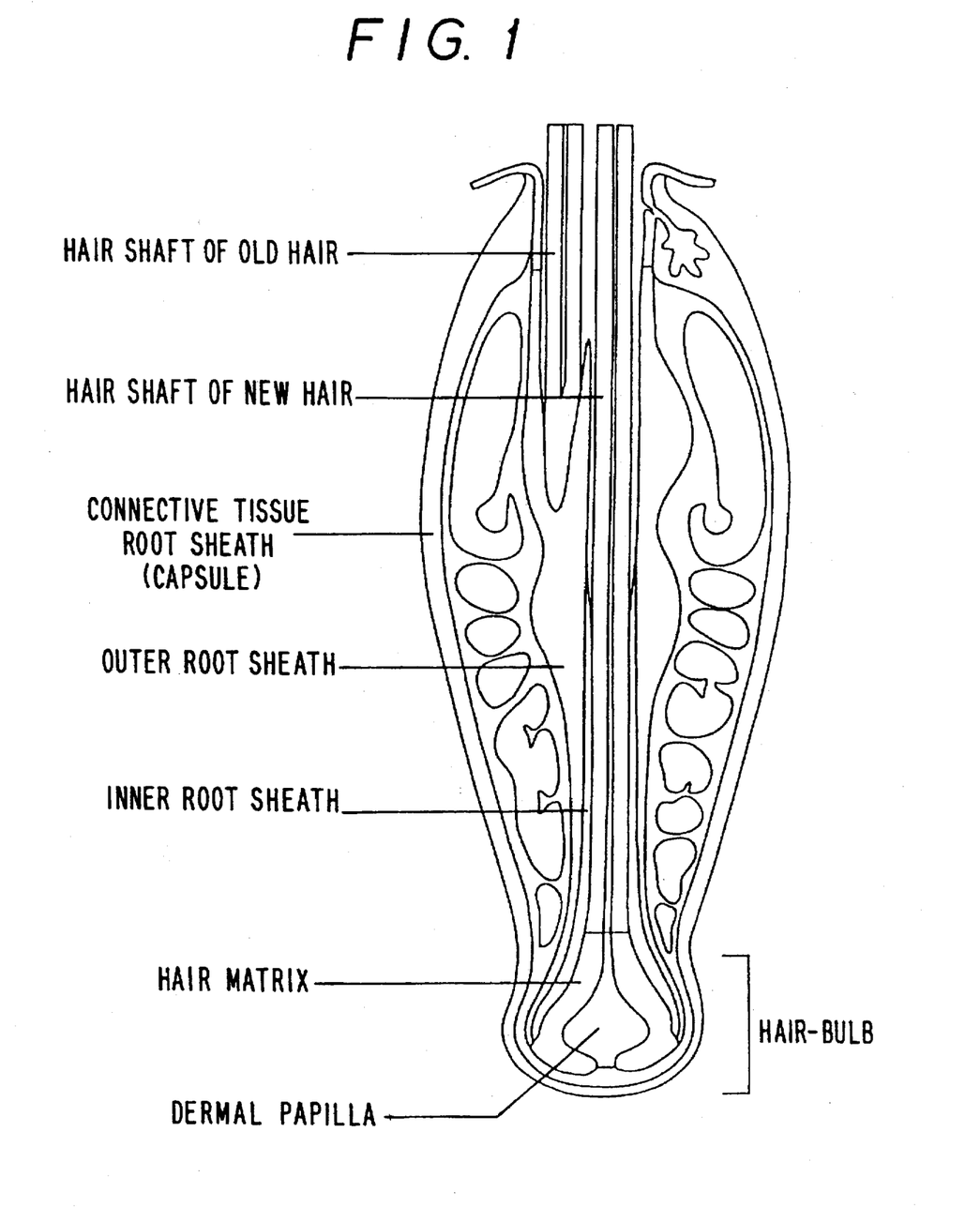
FIG. 1 is diagrammatic representation of the whisker follicle of rats.

The part of the hair base embedded in the skin is called the hair follicle and consists of plural different tissues, forming a characteristic structure as shown in FIG. 1. Recently, it has become clear that these tissues are significantly involved in the differentiation and growth of hairs. However, there are still many unknown points with respect to the function of each tissue, and elucidation of differentiation factors and growth factors responsible for exchange of information between the tissues is an important question to be answered in the future.

Figure 2:
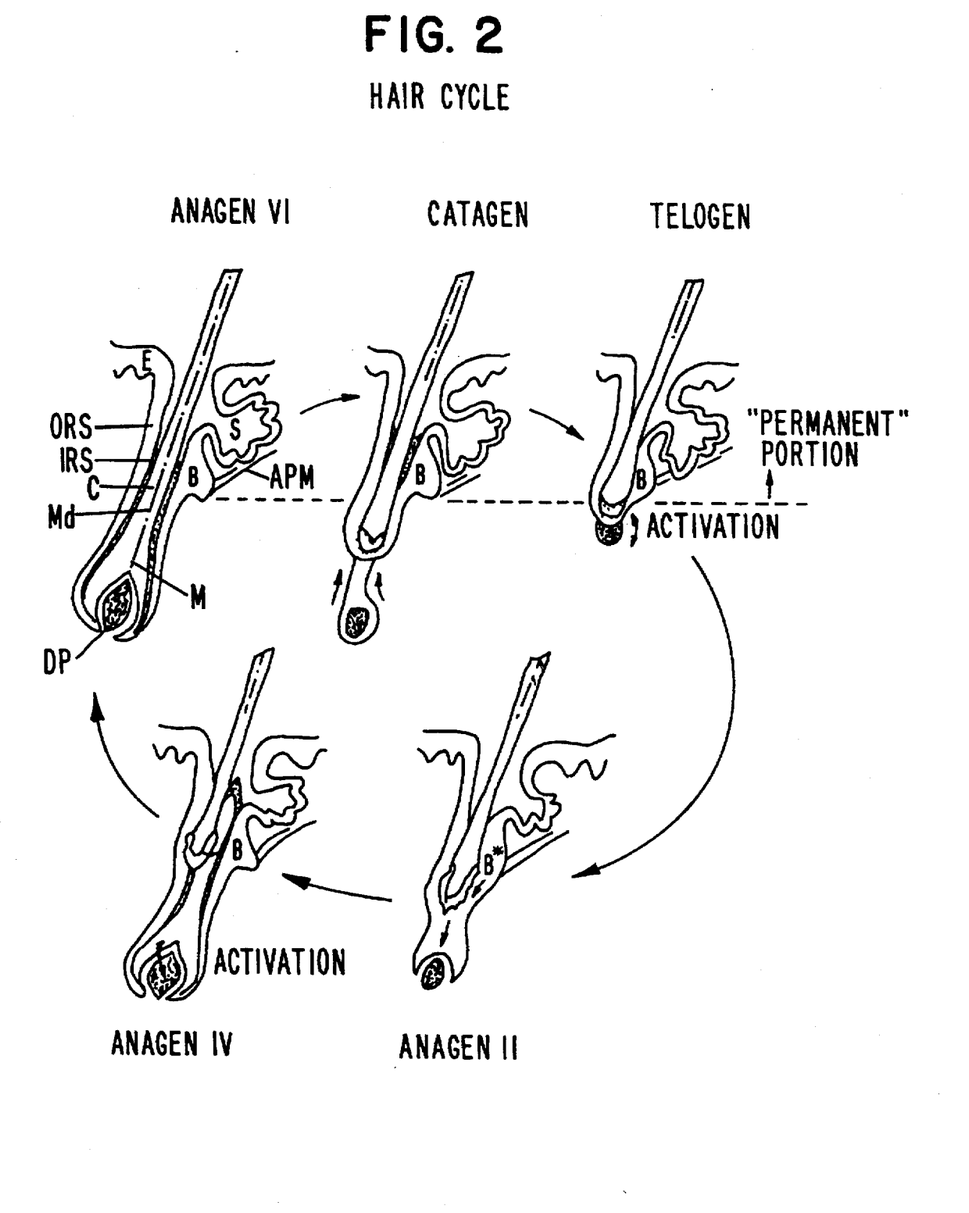
FIG. 2 is diagrammatic representation of the hair follicle indicating the hair cycle.

In general, hair has a rhythm of growth, and, as depicted in FIG. 2, the hair cycle proceeds from the growing stage (anagen) to the degeneration or transition stage (catagen), resting stage (telogen) and the growing stage again. In the growing stage, the whole hair follicle extends to reach the deep region of the skin; the hair matrix, which causes extension of the hair, is formed; and the dermal papilla, which is believed to be necessary for the formation of the hair matrix, develops. In the degeneration or transition stage, the activity of the hair matrix ceases, and the dermal papilla shrinks. Accompanying these changes, the hair follicle shrinks and enters the resting stage. When the hair enters the growing stage again, the dermal papilla is reorganized, followed by extension of the hair follicle and formation of new hair matrix. The ratio of hairs at each stage of the hair cycle differs depending on the age of the individual and the site of the hair. This information can be used as a rough index of the health condition of an individual's hairs.

The ratio of hairs at each stage of the hair cycle has been determined mainly based on observation of the morphology of the hairs. For example, part of the skin is excised and made into thin tissue sections, and the specimens are subjected to image analysis using a computer. The hair cycle stage of each hair follicle is determined on the basis of the length of the hair follicle and the degree of development of tissues, such as the hair matrix and dermal papilla. The data thus obtained are compiled, and a graph called a follicurogram is prepared. Based on the follicurogram thus prepared, the condition of the hair of the subject is assessed. In this method, the stage of the hair cycle of each hair follicle is accurately determined based on the 3-D structure of the hair follicle reconstructed by means of computer image processing of the serial tissue sections. On the other hand, this method is not necessarily simple or convenient, because the method requires expensive equipment, it is necessary to become familiar in judging each stage of the hair cycle, it is necessary to learn the operation method of the equipment.

Unlike the above method, the immunohistochemical method using antibodies has been well established as a general and routine test method for diagnosis of cancers, etc. Therefore, if a monoclonal antibody specific for each tissue of the hair is available and applied to the immunohistochemical method, such method is expected to provide physicians and researchers with a simple and convenient method for testing the stage of the hair cycle and to be useful for the elucidation of the causes of such diseases as abnormal hair development and alopecia.

For the reasons described above, a variety of antibodies that react with the hair follicle have been developed and reported. Many of the said antibodies are those against keratin or extracellular matrix components. Keratin is a group of proteins known as the major component of the nail and hair, and more than 20 similar proteins are known as keratin. Keratin is known to distribute to specific tissues (e.g., Genes & Develop., 3, p 1–5, 1989). Antibodies against components of extracellular matrix, such as those against Type I–IV collagen, fibronectin, laminin, chondroitin sulfate, etc., have been prepared, and many of these have already been commercialized.

However, each of these conventional antibodies was prepared using the pertinent purified protein as the antigen, while nothing has been known with respect to the method for preparing hybridomas producing a monoclonal antibody recognizing specific tissue of the hair follicle without any purification of target antigens.

SUMMARY OF THE INVENTION

The objectives of this invention are to provide monoclonal antibodies capable of specifically recognizing a specific tissue of the hair follicle, hybridomas producing the said antibodies, and a method for preparing the hybridomas.

That is, this invention provides a method for preparing hybridomas producing monoclonal antibodies against the hair follicle tissue, which comprises the steps of:

(a) quickly and deeply freezing hair-bulb of follicle isolated from a human or an animal of species A;

(b) immunizing an animal of species B by subcutaneously administering the hair-bulb of being thawed out to said animal;

(c) re-immunizing said animal by intravenously and intraperitoneally administering liquid and solid components of the hair-bulb which are obtained with centrifugation of the thawed hair-bulb to said animal;

(d) fusing spleen cells or lymphoid cells isolated from the immunized animal with myeloma cells derived from an animal of species B or C; and (e) cloning fusion cells which produce antibodies capable of specifically binding to the hair follicle of human or animal of species A.

This invention also provides hybridomas prepared by the above-described method and monoclonal antibodies that are produced by the said hybridomas and characterized by their ability of specifically recognizing human hair follicle tissue.

According to this invention, monoclonal antibodies specifically recognizing each tissue of human hair follicle are provided. These monoclonal antibodies enable functional analysis of each tissue of the hair follicle and specific determination of the stage of the hair cycle, and they also enable development of new diagnostic methods, therapeutic methods, therapeutic drugs for abnormal hair development, alopecia, etc.

DETAILED DESCRIPTION OF THE INVENTION

The present inventors have conducted studies to achieve the above-described objectives. As a result, they found that it is possible to efficiently obtain hybridomas producing monoclonal antibodies against different antigens (hair follicle tissues) by freezing and thawing part of the hair follicle tissue, followed by administering the resultant tissue as it is to animals to immunize the animals. On the basis of this finding, they have completed this invention. A detailed description of this invention is explained below.

(1) Preparation of hybridomas

Hybridomas obtained by this invention can be prepared in accordance with a well known method (for example, Nature, 258, p 495, 1975), except for the method for immunizing animals. In the following descriptions, the hair-bulb of whisker follicle of rats is used as a source of immunization, and mice are used as an animal to be immunized.

1) Immunization of animal

Mice are immunized in accordance with the following procedures. That is, hair-bulbs (the lower part of the whisker follicle wherein the dermal papilla, hair matrix, etc., are present) of hair follicle isolated from rats is frozen once and then thawed. 20 to 30 hair-bulbs are subcutaneously embedded on each side of the back of a mouse to immunize the mouse. After 46 days, the hair-bulbs similarly frozen and thawed are finely minced, centrifuged, and the mouse is immunized again by intravenously injecting the supernatant (liquid component) and intraperitoneally administering the solid pellet (solid component) suspended in physiological saline to the mouse.

2) Cell fusion

Spleen cells or B lymphocytes isolated from the immunized mouse are fused with mouse myeloma cells by an ordinary method to obtain fused cells. Several cell fusion methods are known. For example, a method using polyethylene glycol, electrofusion, etc., can be used. In this invention, any of these methods can be used to obtain fused cells.

3) Screening

Using the supernatant of fused cells culture obtained by one of the above method, the reactivity of the supernatant with the hair follicle tissue of rats is determined by means of a known immuno-histochemical method, etc., thereby selecting monoclonal antibody-producing cells.

4) Cloning

In order to obtain a homogeneous cell population deriving from one clone from the specific antibody-producing cells selected in the above, cloning is performed by means of the known limiting dilution, etc., and a cell strain which stably produces the desired monoclonal antibody, i.e. the so-called hybridoma, is obtained.

Hybridomas of this invention prepared by the above-described method have functional characteristics of being capable of producing monoclonal antibodies specifically recognizing different constituents of the hair follicle tissue.

(2) Acquisition of antibodies

Antibodies of this invention can be purified by an ordinary biochemical technique employed for purification of proteins from the supernatant of a culture of above-described hybridomas or from ascites obtained by intraperitoneally inoculating said hybridomas to animals followed by in vivo cultivation of the hybridoma.

Antibodies of this invention are characterized in that the antibodies are those which have been selected from among several monoclonal antibodies obtained by the above method and which have been confirmed to be capable of specifically recognizing different constituents of the hair follicle.

Monoclonal antibodies of this invention are applicable, but not exclusively, to various kinds of immunological determination, such as detection and quantification of hair follicle using the antigen-antibody reaction, histoimmunostaining, western blotting, etc.

The following examples are presented to explain this invention in more detail and concretely, but this invention is not defined by these examples.

EXAMPLES

Example 1

(Preparation of hybridomas)

(1) Preparation of antigen

The whole upper lip region of 8-weeks-old rats was excised and immersed in D-MEM medium. Each whisker follicle was isolated by picking it from the reverse side of the lip with a forceps and pulling it off the lip. The hair-bulb of the lower part of the whisker follicle was cut away from each hair follicle using a knife, and the hair-bulbs thus collected were preserved at −80° C.

(2) Primary immunization

Using a 16-gauge injection needle, a hole was created on both sides of the back of 7-week-old BALB/c mice, hair-bulbs thawed at room temperature were placed in a plastic catheter, and 25 hair bulbs were subcutaneously inoculated into each hole by pushing them out through the catheter.

(3) Booster immunization

Forty-six days after the first immunization, 25 hair-bulbs were thawed and finely minced in physiological saline using a pair of dissecting scissors. The hair-bulb suspension was centrifuged, and the liquid component (supernatant; 300 µl) was intravenously injected, while the solid component (pellets) was suspended in 1 ml of physiological saline and intraperitoneally administered (adjuvant was used).

(4) Cell fusion

On the third day after the booster immunization, cell fusion was performed using NS-1 myeloma cells in accordance with the ordinary method, and 147 fused cells were obtained.

(5) Screening and cloning

Culture supernatants of fused cells were immunohistochemically screened on the basis of their responsiveness against frozen sections of whisker follicles, and cells exhibiting a high response were cloned.

As a result, hybridoma strains of 18 clones of 14 kinds were obtained.

The above-described immunohistochemical screening was performed as follows. That is, frozen sections of whisker follicles of rats were prepared, air-dried for about one hour, washed with PBS (phosphate-buffered salt solution) (5 min×3 times), covered with 5% rabbit normal serum, and stood for 30 min. Then, the rabbit serum was removed, and the sections were covered with the supernatant (250 μl) of each cultured hybridoma for one hour, briefly rinsed with PBS, washed with PBS (5 min×3 times), and allowed to react with the secondary antibody labeled with peroxidase (100-times diluted anti-IgG antibody, 300-times diluted anti-IgM antibody; Cappel Co.). Next, the sections were washed with PBS (5 min×3 times), subjected to color development with a diaminobenzidine solution, washed with distilled water (5 min×3 times), subjected to hematoxylin staining, washed with distilled water, dehydrated with alcohol, cleared with xylene, and embedded. Staining patterns of these sections were inspected under a microscope, and cells producing antibodies were selected.

clonal antibodies (K1301–1306, 1308–1318 and 1321) were obtained by purifying the supernatant of each culture.

These monoclonal antibodies were tested for their specificity for whisker follicle of rats. The results are presented in Table 1. Five antibodies, K1301, K1302, K1308, 1313 and K1314, exhibited specific reaction with mesenchymal cells, such as the dermal papilla, root sheath of connective tissue (capsule), vascular sinus, etc. Because the reaction specificity of these five antibodies is very similar to each other, it is very likely that they are the same antibody. K1311 also reacted strongly with mesenchymal cells, but its reaction with the root sheath of connective tissue was not strong. K1316 tended to react with blood components. K1317 reacted strongly with the keratinized layer. Clones other than these mainly reacted with the epithelial cells.

TABLE 1

| Antibody | Dermal papilla | Connective tissue root sheath | Vascular sinus | Arrector pili muscle | Subaceous grand | Hair matrix | Hair shaft | | |
|---|---|---|---|---|---|---|---|---|---|
| | | | | | | | Medulla | Cortex | Cuticle |
| K1301 | ++ | ++ | ++ | [+] | +/− | − | [+] | − | − |
| K1302 | ++ | ++ | ++ | [+] | +/− | − | [+] | − | − |
| K1308 | ++ | ++ | ++ | [+] | − | − | ND | − | − |
| K1313 | ++ | ++ | ++ | [+] | +/− | − | ND | − | − |
| K1314 | ++ | ++ | ++ | [+] | +/− | − | [+] | − | − |
| K1311 | ++ | [+] | ++ | − | + | − | [+] | − | − |
| K1303 | − | − | + | ++ | + | +/− | − | [+] | [++] |
| K1306 | +/− | − | + | ++ | + | + | − | [++] | [++] |
| K1309 | − | − | +/− | − | + | +/− | − | [+] | [+] |
| K1305 | +/− | + | ++ | − | +/− | + | +/− | [++] | − |
| K1315 | +/− | +/− | + | [+] | +/− | + | − | + | +/− |
| K1321 | +/− | +/− | +/− | − | − | + | +/− | + | [+] |
| K1318 | − | − | − | ND | +/− | − | − | − | − |
| K1312 | +/− | − | + | − | + | − | − | − | − |
| K1304 | − | [+] | ++ | − | + | − | − | − | − |
| K1310 | − | − | +/− | − | + | ++ | − | [++] | [+] |
| K1316 | [+] | − | ++ | − | − | − | − | − | − |
| K1317 | +/− | − | +/− | − | − | + | − | + | [++] |
| NC[M] | − | +/− | + | − | +/− | − | − | − | − |
| NC[G] | − | +/− | +/− | − | − | − | − | − | − |

| Antibody | Inner root sheath | | | Outer root sheath | | | | |
|---|---|---|---|---|---|---|---|---|
| | Inner root sheath cuticle | Huxley's layer | Henle's layer | Innermost layer of outer root sheath | Lower outer root sheath | Upper outer root sheath | Pore portion | Basal membrane |
| K1301 | − | − | − | − | − | − | − | ++ |
| K1302 | − | − | − | − | − | − | − | ++ |
| K1308 | − | − | − | − | − | − | − | ++ |
| K1313 | − | − | − | − | − | − | − | ++ |
| K1314 | − | − | − | − | − | − | − | ++ |
| K1311 | − | − | − | − | − | [+] | [+] | − |
| K1303 | − | − | − | [++] | − | − | [+] | |
| K1306 | +/− | +/− | + | [++] | − | − | [+] | |
| K1309 | − | ++ | ++ | [++] | − | − | − | |
| K1305 | + | + | + | ++ | + | ++ | − | |
| K1315 | + | + | ++ | ++ | +/− | + | [+] | |
| K1321 | + | +/− | + | − | ++ | ++ | ++ | |
| K1318 | ++ | +/− | + | − | − | [++] | ++ | |
| K1312 | − | + | ++ | − | +/− | [+] | + | |
| K1304 | − | − | − | − | − | [++] | − | |
| K1310 | − | − | − | − | − | [+] | [+] | |
| K1316 | − | − | − | − | − | − | − | |
| K1317 | − | − | − | + | − | [+] | [++] | |
| NC[M] | − | − | − | − | − | − | − | |
| NC[G] | − | − | − | − | − | − | − | |

Example 2

(Acquisition of monoclonal antibodies)

Each of the hybridomas prepared in Example 1 was cultured by the ordinary method, and 18 kinds of mono- Example 3

(Acquisition of monoclonal antibody against human hair follicle)

The 18 kinds of hybridomas obtained in Example 2 above were screened again for their reaction with frozen sections of human scalp by Immunohistochemical method. As a result, 10 kinds of hybridomas producing antibodies reacting with human scalp hair follicular tissues were obtained. The reaction specificity of monoclonal antibodies produced by these hybridomas against human scalp hair follicular tissues was almost the same as those against rat whisker follicular tissues. The reaction specificity of each of six of the 10 kinds of hybridomas is presented below (the number of + symbols indicates the magnitude of the reaction). In order to unify the number, the hybridomas are given a serial number after a code of YMP-HF. In addition, the site of response to each antibody was presented with underlines in FIGS. 3–8.

Figure 3:
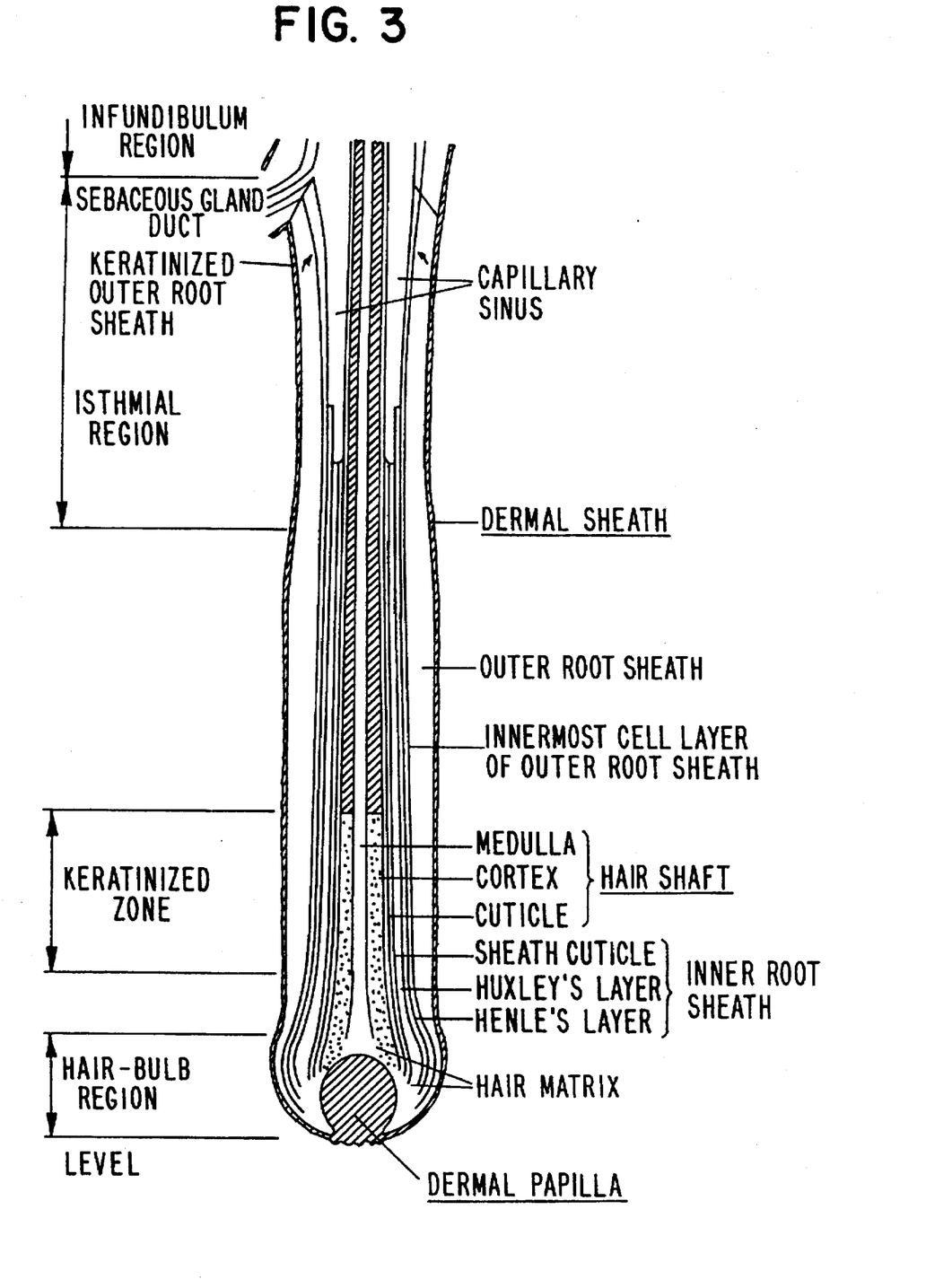
FIGS. 3–8 are diagrammatic representation of the human hair follicle indicating sites of reaction (underlined) with monoclonal antibodies YMP-HF1–6 prepared by this invention respectively.

(1) YMP-HF1 (see FIG. 3; K1311)

Dermal papilla: ++

Hair shaft: +

Figure 4:
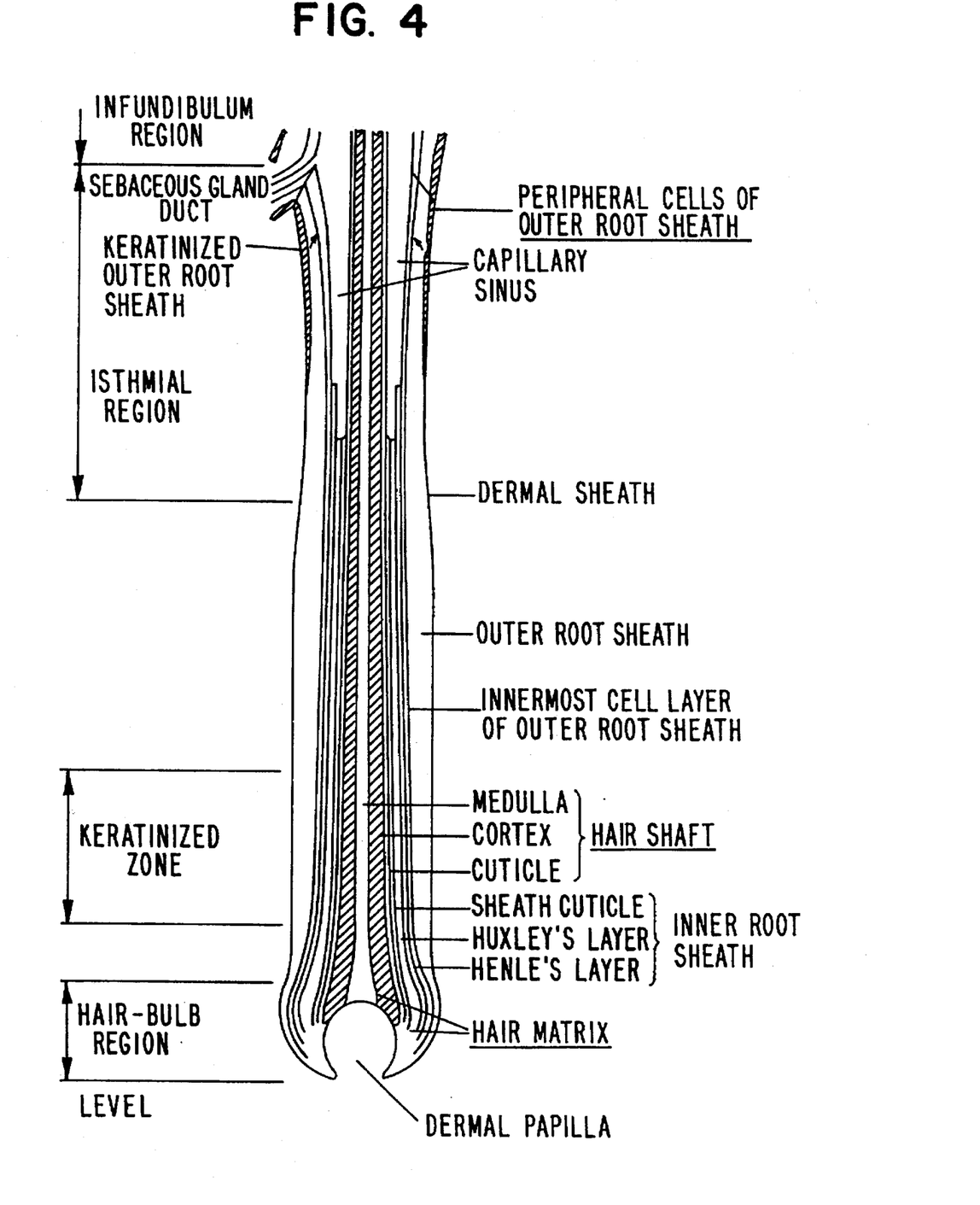

(2) YMP-HF2 (see FIG. 4; K1310)

Hair shaft: +++

Hair matrix: ++

Outer root sheath: + (responded only to cells in the upper external periphery)

Figure 5:
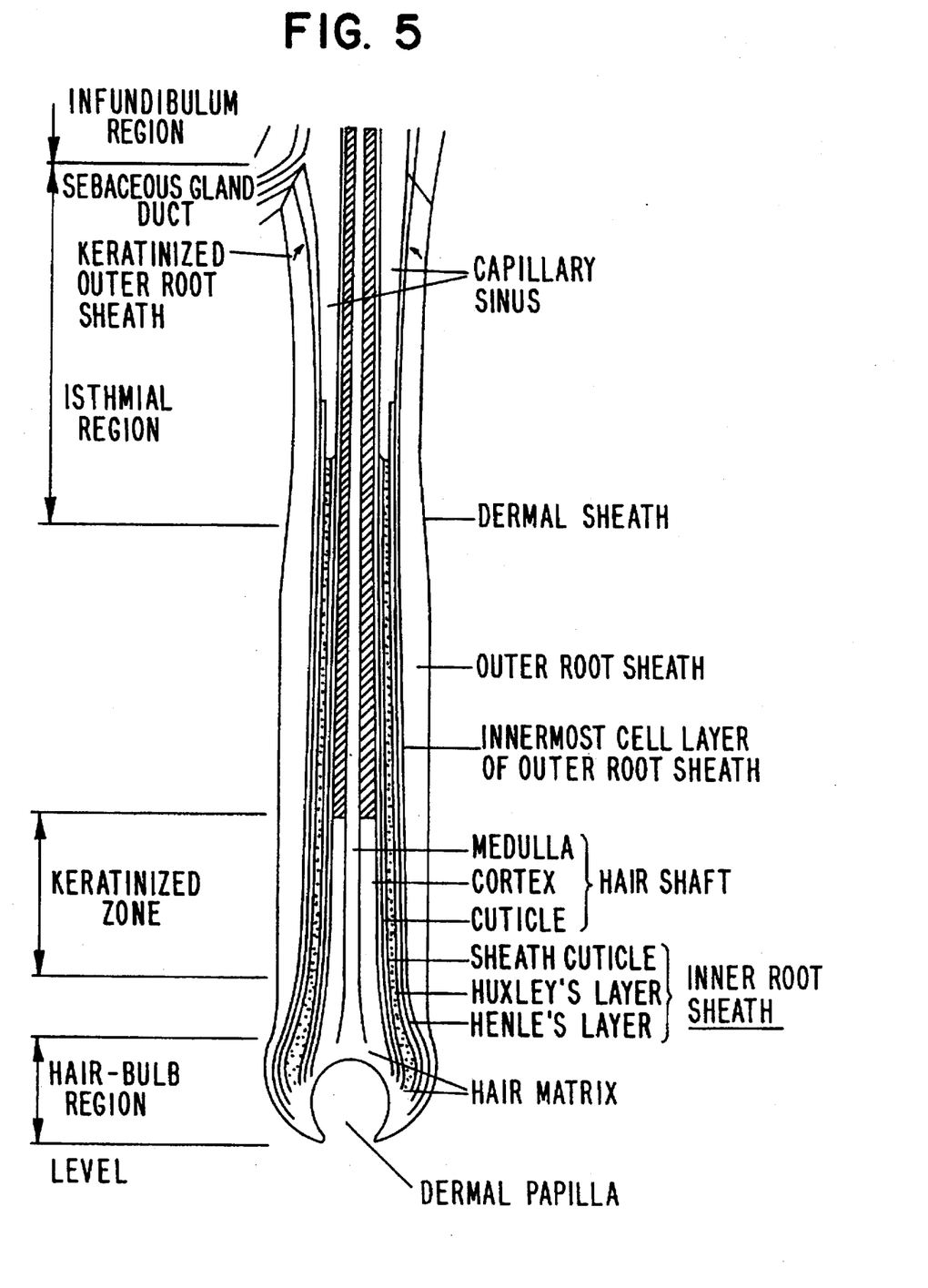

(3) YMP-HF3 (see FIG. 5; K1312)

Inner root sheath: +

Figure 6:
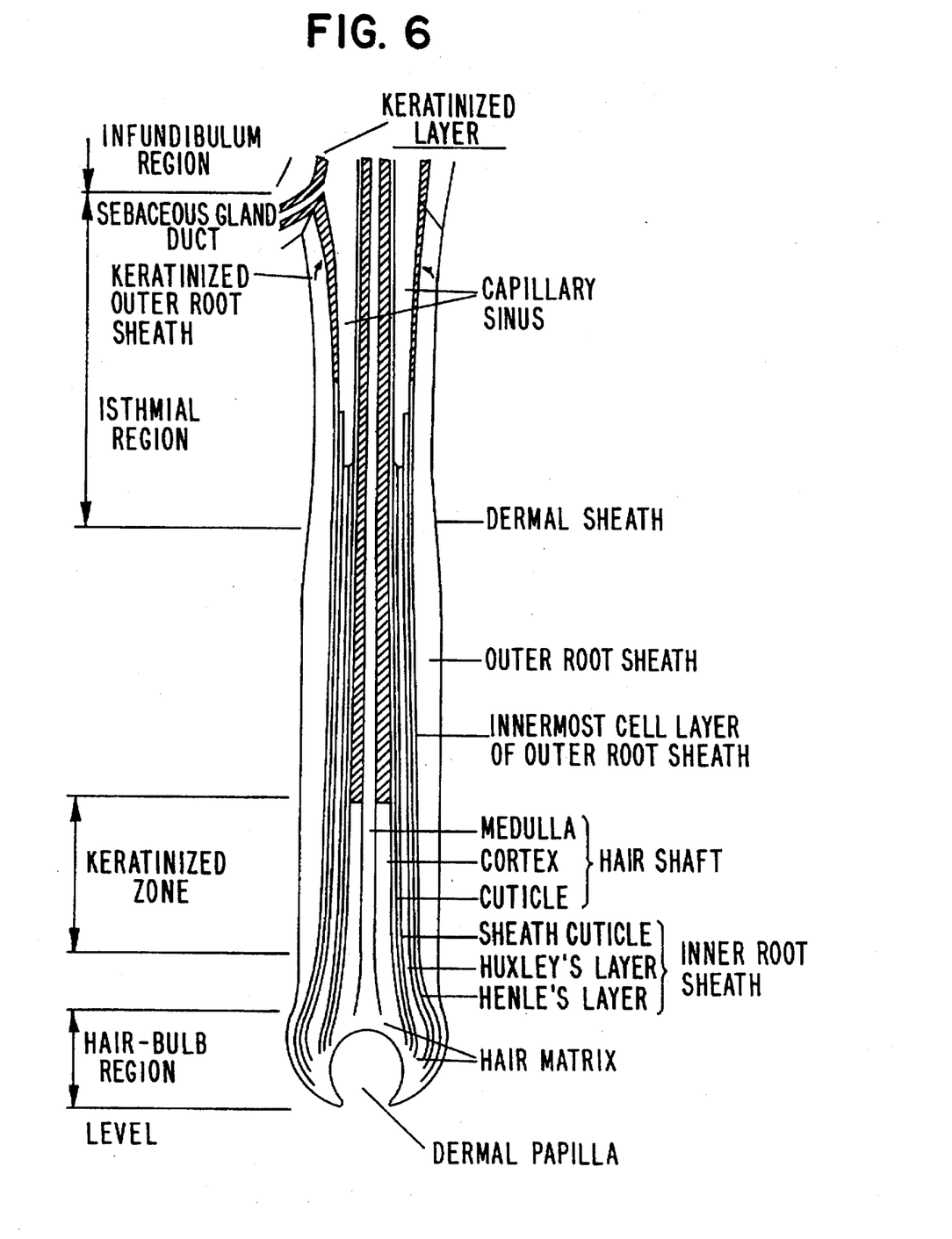

(4) YMP-HF4 (see FIG. 6; K1317)

Keratinized layer of outer root sheath: +++ (similarly responded to the keratinized layer of the skin)

Figure 7:
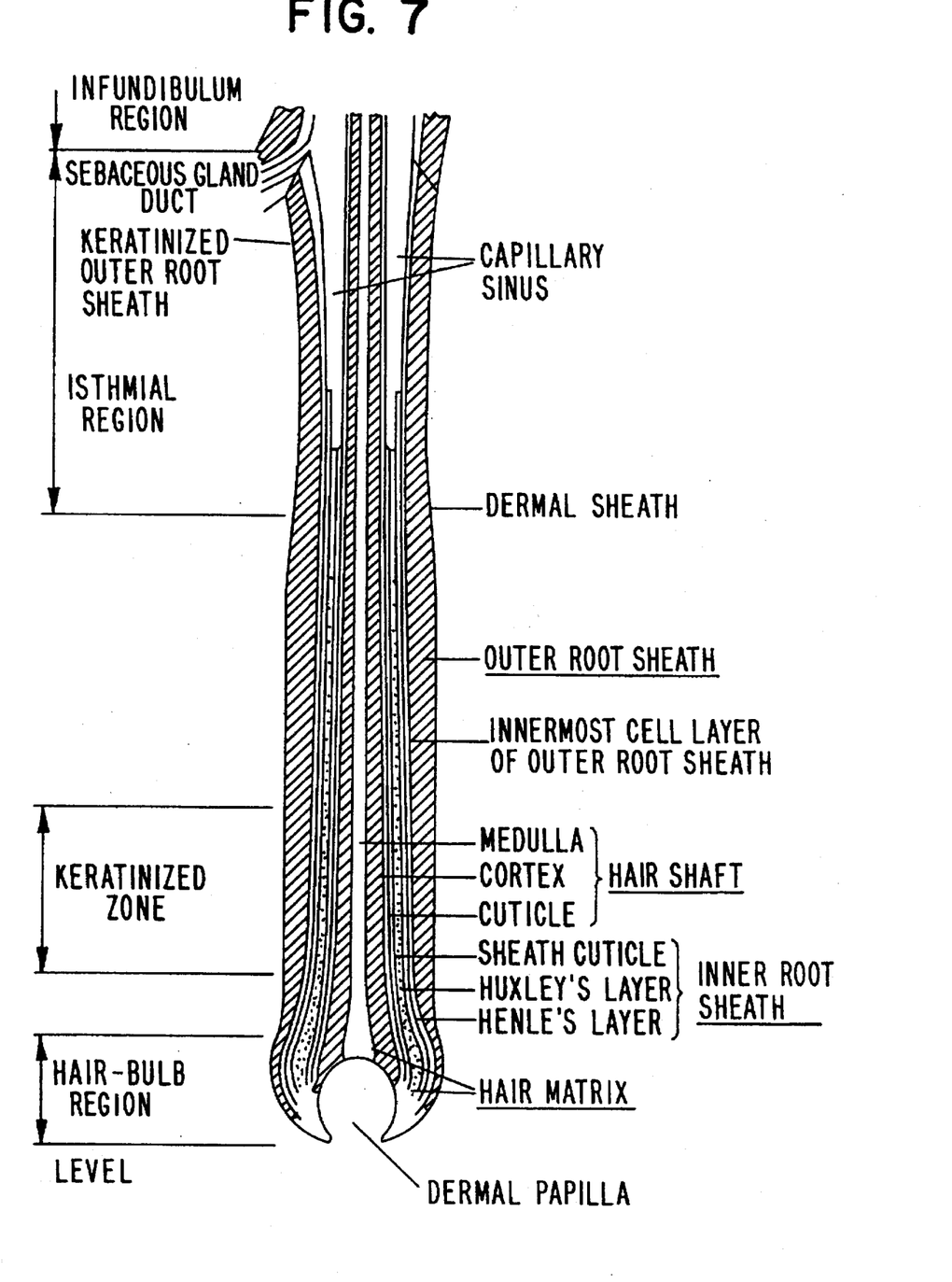

(5) YMP-HF5 (see FIG. 7; K1321)

Hair shaft: ++

Hair matrix: +

Outer root sheath: +++

Inner root sheath: + (did not respond to keratinized sheath)

Figure 8:
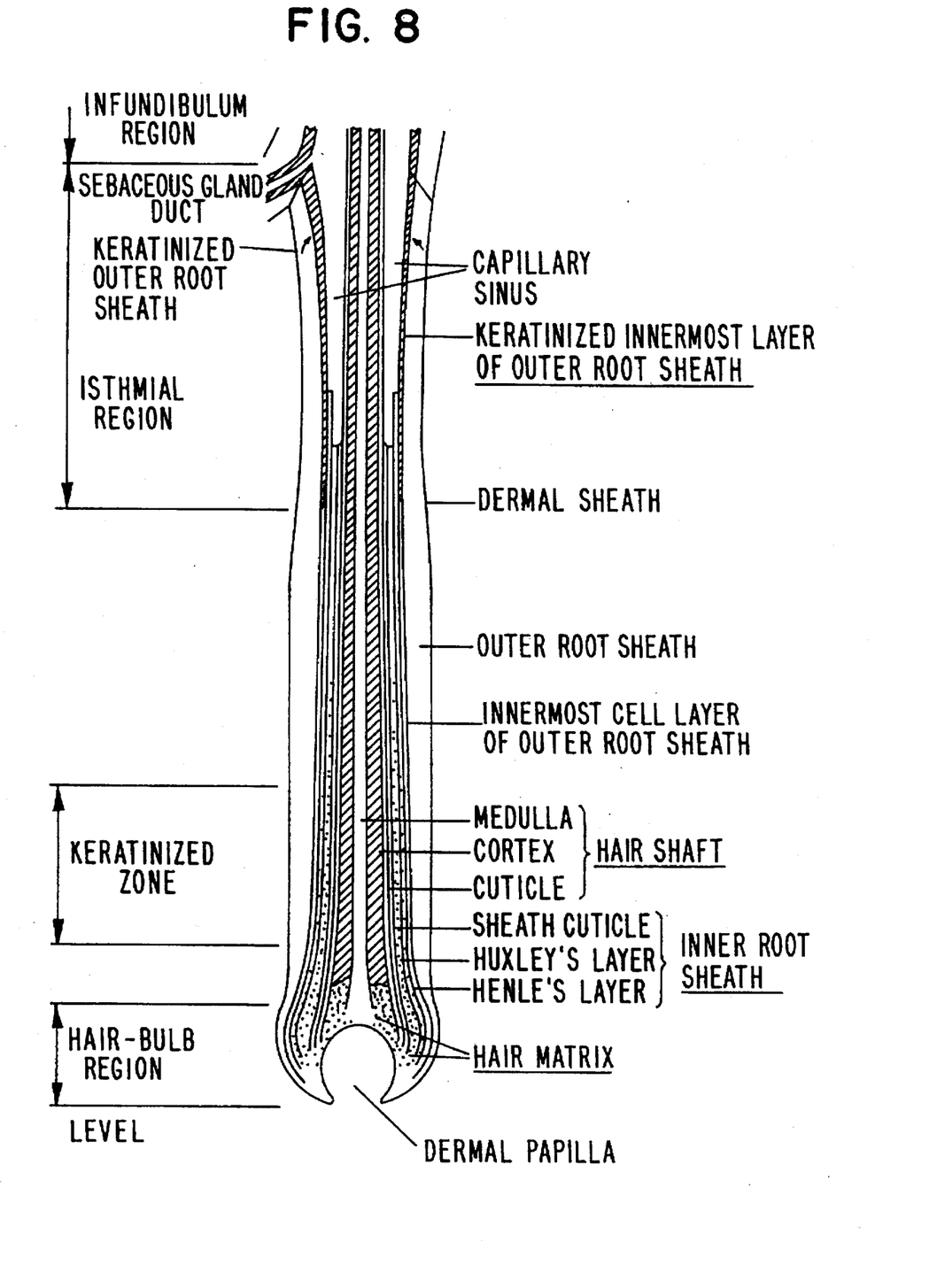

(6) YMP-HF6 (see FIG. 8; K1303)

Hair shaft: ++

Hair matrix: +

Innermost layer of outer root sheath: ++ (responded to keratinized sheath)

Inner root sheath: +

As described above, an antibody mainly recognizing the dermal papilla (YMP-HF1), an antibody mainly recognizing the lower hair shaft and the outer root sheath (YMP-HF2), an antibody mainly recognizing the inner root sheath (YMP-HF3), an antibody mainly recognizing the outer root sheath and hair shaft (YMP-HF5), and an antibody mainly recognizing the innermost layer of the outer root sheath and hair shaft (YMP-HF6) were obtained.

We claim:

1. A method for preparing a hybridoma that produces a monoclonal antibody which specifically binds to a target hair follicle tissue of a subject human or animal, comprising the steps of:

(a) freezing hair-bulbs of hair follicles isolated from the subject human or animal;

(b) immunizing a host animal, wherein said host animal is a mouse, by subcutaneously embedding a first portion of the hair-bulbs into the host animal, wherein the hair-bulbs are thawed out prior to being embedded;

(c) reimmunizing the host animal with a second portion of the hair-bulbs, the hair-bulbs prior to immunization being thawed, minced, suspended in a liquid and centrifuged to obtain a liquid supernatant and a solid component after centrifugation, the host animal being reimmunized by intravenously administering the liquid supernatant of the hair-bulbs, and by intraperitoneally administering the solid component of the hair-bulbs, to the host animal;

(d) fusing spleen cells or lymphoid cells isolated from the immunized host animal with myeloma cells to obtain hybridoma cells; and     (e) screening the hybridoma cells to isolate a hybridoma cell that produces a monoclonal antibody which specifically binds to the target hair follicle tissue of the subject human or animal.

2. The method according to claim 1, wherein the subject animal is rat.

\* \* \* \* \*